United States Patent
Aceti

[11] Patent Number: 5,979,589
[45] Date of Patent: *Nov. 9, 1999

[54] FLEXIBLE HEARING AID

[75] Inventor: John G. Aceti, Cranbury, N.J.

[73] Assignee: Sarnoff Corporation, Princeton, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/850,670

[22] Filed: May 2, 1997

[51] Int. Cl.⁶ ........................................... A61B 7/02
[52] U.S. Cl. ............................. 181/135; 381/328
[58] Field of Search ...................... 181/130, 135; 381/322, 328; 128/84, 865, 867

[56] References Cited

U.S. PATENT DOCUMENTS

| | | | |
|---|---|---|---|
| 2,430,229 | 11/1947 | Keysey | 181/135 |
| 2,487,038 | 11/1949 | Baum | 181/135 |
| 2,939,923 | 6/1960 | Henderson | 381/68.6 |
| 2,987,584 | 6/1961 | Webber et al. | 381/68.6 |
| 3,080,011 | 3/1963 | Henderson | 181/135 |
| 3,527,901 | 9/1970 | Gelb | 179/107 |
| 3,598,928 | 8/1971 | Hickox | 381/322 |
| 4,869,339 | 9/1989 | Barton | 181/130 |
| 4,870,688 | 9/1989 | Voroba et al. | 381/60 |
| 5,002,151 | 3/1991 | Oliveira et al. | 181/130 |
| 5,068,902 | 11/1991 | Ward | 381/68.6 |
| 5,185,802 | 2/1993 | Stanton | 381/68.6 |
| 5,606,621 | 2/1997 | Reiter et al. | 381/68.6 |
| 5,654,530 | 8/1997 | Sauer et al. | 181/130 |

*Primary Examiner*—Khanh Dang
*Attorney, Agent, or Firm*—William J. Burke

[57] ABSTRACT

An earmold for a hearing aid includes a cylindrical tube of a soft, pliable material having a cylindrical passage therethrough. A plurality of conical fins project outward from the tube and are along the entire length of the tube. A pull is secured to and extends from one end of the tube.

11 Claims, 1 Drawing Sheet

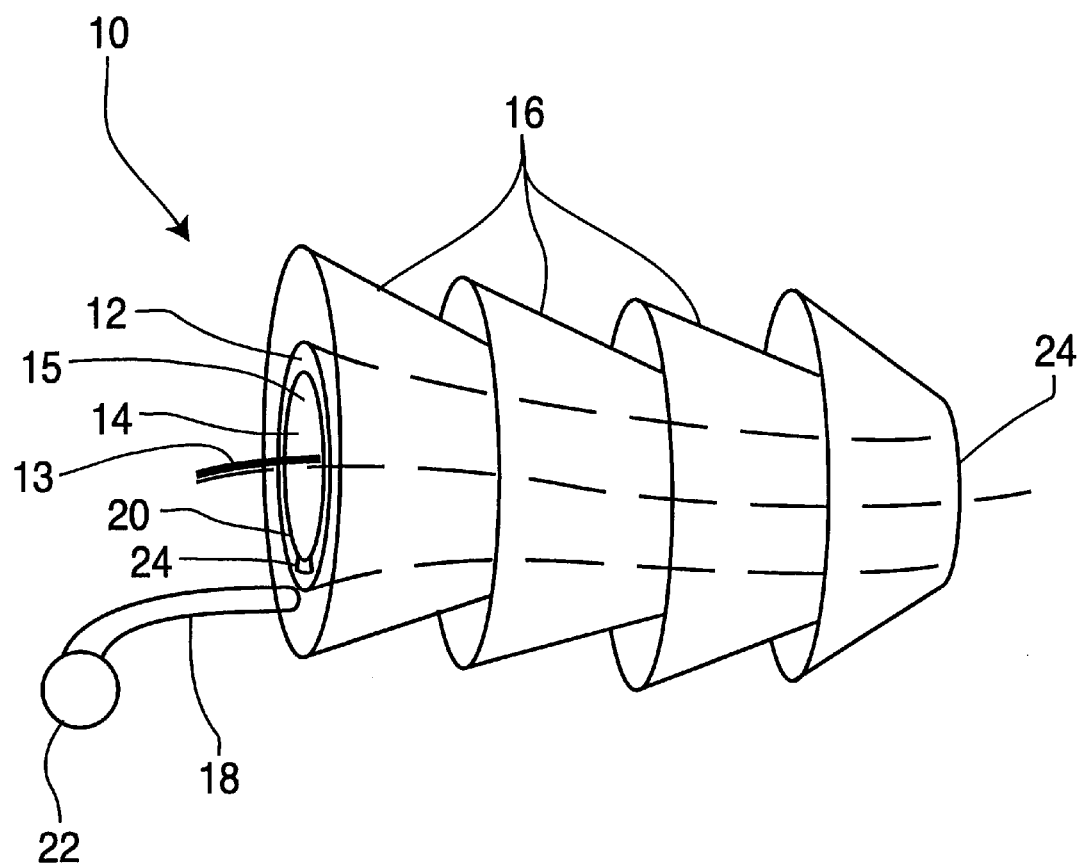

FLEXIBLE HEARING AID

FIELD OF THE INVENTION

The present invention relates to an earmold for a hearing aid, and, more particularly to a generic earmold for a hearing aid which fits tightly and comfortably in the canal of the ear of various sizes and shapes.

BACKGROUND OF THE INVENTION

Most hearing aids include an earmold which is inserted and retained in the canal of the ear of the user. The earmold may contain the electronics of the hearing aid, including the speaker, or may be connected to the electronics, which are outside the canal of the ear, by a tube. The earmold must fit comfortably in the ear and must be formed in a manner that it is readily retained in the canal of the ear. Retention of the earmold in the canal of the ear can be accomplished by friction and/or mechanical locking. Friction is created by radial pressure of the earmold on the wall of the canal. The more pressure, the greater is the retention force. However, friction is also dependent on lubricants between the earmold and the wall of the canal. The presence of cerumen (ear wax), perspiration or water significantly reduces friction retention. Therefore, mechanical locking is the primary means by which most hearing aids are retained in the ear. For mechanical locking, the earmolds are molded to fit the complex shape of the ear canal. These complex interlocking shapes hold the hearing aid in place without relying on friction so that they are not susceptible to the loosening caused by forces which tend to dislodge the hearing aid. However, the making of these complex interlocking shapes is a laborious, inaccurate and time consuming process which often requires the user to make several visits to the audiologist or dispenser before an earmold with a secure fit can be made. This is not only time consuming, but also greatly increases the cost of the hearing aid.

Another problem which arises in hearing aids is acoustic feedback. Acoustic feedback occurs when amplified sound from the hearing aid's speaker enters the microphone and is subsequently re-amplified, resulting in a squealing noise. If the earmold fits well, it attenuates the sound sufficiently to prevent feedback. Therefore, a good fit of the earmold in the canal of the ear is desirable to minimize acoustic feedback. It has been demonstrated that soft earmolds are superior to hard earmolds in the reduction of feedback. However, the earmolds generally used which are specifically shaped to fit a particular ear canal are generally made of a hard material. This provides an earmold which has a longer life and which can be easily removed and reinserted for cleaning and repair.

Two of the more recent attempts at commercializing preformed earmolds are shown in U.S. Pat. No. 4,870,688 to B. Voroba et al., issued Sep. 26, 1989, entitled MASS PRODUCTION AUDITORY CANAL HEARING AID, and U.S. Pat. No. 5,002,151 to R. J. Oliveira et al., issued Mar. 26, 1991, entitled EAR PIECE HAVING DISPOSABLE, COMPRESSIBLE POLYMERIC FOAM SLEEVE. The earmold shown in the patent to Oliveira et al. uses a compressible retard recovery foam that can be compressed and then inserted into a person's ear, and allowed to recover to fill into the canal. This earmold is held in only by friction. Also, the earmold is connected to the electronics by a tube which has the tendency to pull on the earmold frequently and thus dislodge it. For this reason, these devices are limited to short trial periods.

The hearing aid shown in the patent to Voroba et al. uses a soft polymeric material in solid form. The earmold is designed to utilize both friction and mechanical locking. However, the earmold contains the electronics and the weight and cantilever of the hear aid dislodges the earmold over time. To support the cantilever, the Voroba et al. earmold is designed to fill in the canal and the concha. However, making a generic earmold which fits well both the canal and the concha is difficult. Also, the earmold of Voroba et al. is designed for several years of use, requiring that it be made of a harder material.

SUMMARY OF THE INVENTION

An earmold for a hearing aid includes a tube of a soft, pliable material. A plurality of fins project outwardly from the tube.

BRIEF DESCRIPTION OF THE DRAWING

The Figure of the drawing is a perspective view of an earmold of the present invention.

DETAILED DESCRIPTION

Referring to the Figure of the drawing, the hearing aid earmold of the present invention is generally designated as 10. Earmold 10 comprises a cylindrical tube 12 of a soft pliable material having a cylindrical passage 14 therethrough. A plurality of conical fins 16 project radially outwardly from the tube 12 and are along the entire length of the tube 12. An integral pull 18 extends from an end 20 of the tube 12. The pull 18 has a knob 22 on its end. A canal 24 is in the surface of the passage 14 and extends the fill length of the tube 12.

The earmold 10 is molded from an elastomer to assure to assure softness, durability and ease of use. Although various materials may be used to make the earmold 10, a preferred material is a heat cured silicone, which has an ideal combination of softness, durability, stability and demonstrated biocompatibility. Thermoplastic elastomers have the processability of thermoplastics and the performance properties of thermoset rubber. Also, thermoplastic elastomers cost one-tenth to one-twentieth the cost of silicone materials. Another advantage of thermoplastic elastomers is their appearance and feel. Most are available in opaque, translucent or colorable grades and possess a smooth, warm feel.

In the use of the earmold 10 of the present invention, the entire electronics of the hearing aid may be inserted in the cylindrical passage 14. The electronics, including microphone, speaker, battery and the amplifier integrated circuit, may be mounted on a flexible printed circuit board 13 which is inserted in a hollow tube 15. The tube 15 would then be inserted in the passage 14 of the earmold 10. The tube 15 could be slightly larger in diameter than the passage 14 so as to have a tight fit therein. Also, the tube 15 could have a detent fitting in a recess in the wall of the passage 14 so as to secure the tube 15 in the earmold 10. Alternatively, the electronics could be outside the earmold and connected to the earmold by a tube, such as shown in U.S. Pat. No. 5,002,151 to Oliveira et al.

The earmold 10, being very compliable, conforms to the general shape of the hollow tube or casing containing the electronics. It is generally known that the ear canal has two natural bends therein, which are often referred to as the first and second bends. If the electronic casing or shell is designed to have these bends as part of its form, and the earmold conforms to these bends, then the earmold takes on these natural bends which provides for mechanical locking. As the earmold and electronics are pushed into the ear, the outer fins compress as does the ear canal's skin and subcutaneous cartilage. Once the earmold is fully inserted, it has a soft but definite locking effect. The ear canal is then in it normal or uncompressed state, but the earmold's conical fins remain compressed to some degree to hold the earmold firmly in the ear.

To use the earmold 10, the user inserts the earmold 10 into the ear with the end 24 of the tube 12 being inserted first. The user presses on the end 20 of the tube 12 to push it into the ear. As the earmold 10 moves into the ear, the fins 16 gently compress as they travel inwardly. When the earmold 10 reaches the inner canal bend, the earmold 10 tends to lock into place. Thus, the earmold 10 is held in the ear of the user by both friction and mechanically. To remove the earmold 10, the user merely pulls on the pull 18 which is integrally molded on the end 20 of the earmold 10. Thus, the earmold 10 can be easily inserted and removed from the ear. Once in the ear, the earmold is held in the ear by both friction and mechanically. Since the earmold 10 is made of a soft, pliable material, it fits comfortably in the ear.

Venting is a means in earmolds to provide intentional sound leakage and to relieve a feeling of pressure in the ear. The canal 24 in the tube 12 provides for such a leakage. The canal 24 can be small, having a diameter of about 0.6 mm, so that it will make little difference to the frequency response and prevent feedback. However, it will be effective in allowing pressure equalization to reduce the feeling of pressure that many hearing aid users experience. The canal 24 may be enlarged to effect frequency response and further improve the user's overall acoustic benefit.

Thus, there is provided by the present invention an earmold for a hearing aid which is made of a soft, pliable molded material and which has conical fins projecting from its outer surface. This provides an earmold which fits comfortably in the ear and is held in the ear by both friction and mechanically. The earmold can be made in a minimum of different sizes to fit a large variety of sizes of ears. Since the earmold is of a pliable material and has the fins projecting therefrom, one size of the earmold can fit into a large variety of sizes of ears. The earmnold can contain the entire electronics of the hearing aid or can be connected to the electronics which is outside of the earmnold by a connecting tube. In addition, the earmold can be molded easily and inexpensively so that it is disposable.

What is claimed is:

1. A hearing aid, comprising:
   a first tube containing hearing aid electronics, where said hearing aid electronics includes a microphone, a speaker, a battery and signal processing circuitry;
   a second tube of a soft pliable material having an inner open portion which radially expands for receiving and substantially enclosing the first tube of hearing aid electronics; and
   a plurality of fins projecting outwardly from the second tube.

2. The hearing aid of claim 1, wherein fins are along the entire length of the second tube.

3. The hearing aid of claim 1, wherein the fins are conical.

4. The hearing aid of claim 1, wherein the open portion is generally cylindrical and has one of a circular or elliptical cross-section.

5. The hearing aid of claim 1, wherein the second tube has first and second ends, further comprising a cord secured and extending from one end of the second tube.

6. The hearing aid of claim 1, wherein the second tube has first and second ends, and the inner open portion extends from the first end to the second end and includes a canal extending from the first to the second end such that when the first tube of electronics are inserted into the second tube, the canal forms a passageway through which air may pass between the first and second ends of the second tube.

7. The hearing aid of claim 1, wherein the second tube is made of a thermoplastic elastomer.

8. A hearing aid, comprising:
   a first tube containing hearing aid electronics, where said hearing aid electronics includes a microphone, a speaker, a battery and signal processing circuitry
   a second tube made of soft pliable material and having first and second ends, an inside surface, and an inside diameter which expands to receive and substantially enclose the first tube of hearing aid electronics, the second tube having a canal in its inside surface that extends from the first end of the second tube to the second end of the second tube such that when the first tube of hearing aid electronics is inserted into the second tube, the canal forms a passageway through which air may pass between the first and second ends of the second tube; and,
   a plurality of fins projecting outwardly from the second tube.

9. The hearing aid of claim 8, further comprising a cord secured to and extending from one end of the second tube.

10. The hearing aid of claim 8 in which the fins are conical.

11. The hearing aid of claim 8 in which the second tube includes a recess on the inside surface for engaging a detent on the first tube tube of hearing aid electronics, for securing the first tube of hearing aid electronics within the second tube.

\* \* \* \* \*